United States Patent
Kamrava et al.

(10) Patent No.: US 7,033,314 B2
(45) Date of Patent: *Apr. 25, 2006

(54) ENDOSCOPIC DEVICES AND METHOD OF USE

(75) Inventors: Michael M. Kamrava, Los Angeles, CA (US); James McDonald, Monson, MA (US)

(73) Assignee: Fidelitycorp Limited, South Pacific (CK)

( * ) Notice: Subject to any disclaimer, the term of this patent is extended or adjusted under 35 U.S.C. 154(b) by 0 days.

This patent is subject to a terminal disclaimer.

(21) Appl. No.: 10/830,411

(22) Filed: Apr. 21, 2004

(65) Prior Publication Data

US 2004/0225187 A1 Nov. 11, 2004

Related U.S. Application Data

(63) Continuation of application No. 10/044,350, filed on Jan. 11, 2002, now Pat. No. 6,758,806.

(51) Int. Cl.
*A61B 1/00* (2006.01)

(52) U.S. Cl. ............... 600/104; 600/153; 600/136; 600/139

(58) Field of Classification Search ......... 600/104, 600/114, 136, 139, 141, 146, 153, 133
See application file for complete search history.

(56) References Cited

U.S. PATENT DOCUMENTS

| 3,709,214 A | 1/1973 | Robertson |
| 4,203,430 A | 5/1980 | Takahashi |
| 4,534,339 A | 8/1985 | Collins et al. |
| 4,779,612 A | 10/1988 | Kishi |
| 4,836,189 A | 6/1989 | Allred, III et al. |
| 4,846,785 A | 7/1989 | Cassou et al. |
| 4,890,602 A | 1/1990 | Hake |
| 4,911,148 A | 3/1990 | Sosnowski et al. |
| 5,195,979 A | 3/1993 | Schinkel et al. |
| 5,199,417 A | 4/1993 | Muller et al. |
| 5,217,466 A | 6/1993 | Hasson |
| 5,325,845 A | 7/1994 | Adair |
| 5,360,389 A | 11/1994 | Chenette |
| 5,472,419 A | 12/1995 | Bacich |

(Continued)

FOREIGN PATENT DOCUMENTS

DE 3702441 A1 8/1988

(Continued)

OTHER PUBLICATIONS

Itskovitz-Eldor et al., "Assisted implantation: direct intraendometrial embryo transfer," Gynecologic & Obstetric Investigation, vol. 43, No. 2, pp. 73-75, 1997.

(Continued)

*Primary Examiner*—Beverly M. Flanagan
(74) *Attorney, Agent, or Firm*—Blakely Sokoloff Taylor & Zafman LLP (57) ABSTRACT

An apparatus including a handle; a first tubular body coupled to the handle and a second tubular body comprising a polymer material coupled to a distal end of the first tubular body and the distal end defining a guide face, wherein the first tubular body and the second tubular body are co-linearly aligned and collectively define a first lumen therethrough extending from an entry port to the guide face; wherein the second tubular body has a dimension adequate for insertion into a uterus of a human subject, and wherein the guide face comprises an outside diameter less than an outside diameter of the second tubular body. Also, a method of using a hysteroscope having a single operating channel.

9 Claims, 7 Drawing Sheets

U.S. PATENT DOCUMENTS

| | | | |
|---|---|---|---|
| 5,484,422 | A | 1/1996 | Sloane, Jr. et al. |
| 5,656,010 | A | 8/1997 | Li et al. |
| 5,716,321 | A | 2/1998 | Kerin et al. |
| 5,772,628 | A | 6/1998 | Bacich et al. |
| 5,807,239 | A * | 9/1998 | DiBernardo ............... 600/135 |
| 5,843,023 | A | 12/1998 | Cecchi |
| 5,921,956 | A | 7/1999 | Grinberg et al. |
| 5,961,444 | A | 10/1999 | Thompson |
| 6,004,302 | A | 12/1999 | Brierley |
| 6,006,002 | A | 12/1999 | Motoki et al. |
| 6,010,448 | A | 1/2000 | Thompson |
| 6,027,443 | A | 2/2000 | Nag |
| 6,053,899 | A | 4/2000 | Slanda et al. |
| 6,156,566 | A | 12/2000 | Bryant |
| 6,203,533 | B1 | 3/2001 | Ouchi |
| 6,258,070 | B1 | 7/2001 | Kaldany |
| 6,273,877 | B1 | 8/2001 | West et al. |
| 6,280,423 | B1 | 8/2001 | Davey et al. |
| 6,281,013 | B1 | 8/2001 | Grondahl |
| 6,319,192 | B1 | 11/2001 | Engel et al. |

FOREIGN PATENT DOCUMENTS

| | | |
|---|---|---|
| GE | 2118840 A | 3/1983 |
| WO | WO 97/13451 | 4/1997 |
| WO | WO 00/54953 | 9/2000 |

OTHER PUBLICATIONS

Wang, Huaixiu, et al., "Decreased in vitro fertilization and cleavage rates after an equipment error during $CO_2$ calibration," Fertility and Sterility, vol. 73, No. 6, pp. 1247-1249, Jun. 2000.

Lesny, Piotr et al., "Transcervical embryo transfer as a risk factor for ectopic pregnancy," Fertility and Sterility, vol. 72, No. 2, pp. 305-309, Aug. 1999.

Goto, Noda, Y., et al., "Pregnancy achieved by transferring blastocysts in to endometrial stroma in mice," Human Reproduction, vol. 7, No. 5, pp. 681-684, May 1992, Abstract only.

Balmaceda JP, et al., "Hysteroscopy and assisted reproductive technology," Obstet Grynecol Clin North Am, vol. 22, No. 3, pp. 507-518, Sep. 1995, Abstract Only.

Asad M, et al., "Twin pregnancy following transmyometrial-subendometrial embryo transfer for repeated implantation failure," Humam Reproduction, vol. 12, No. 12, pp. 2824-2825, 1997, Abstract Only.

Brunk, D., "Blastocyst transfer cuts multiples risk," Ob.Gyn. News, vol. 35, No. 23.

"Flexible Hysteroscopes," Comtemporary OB/GYN, Apr. 15, 1999, Medical Economics, Montvale, NJ, pp. 6-11.

* cited by examiner

ENDOSCOPIC DEVICES AND METHOD OF USE

CROSS-REFERENCE TO RELATED APPLICATION

This application is a continuation of U.S. patent application Ser. No. 10/044,350, filed Jan. 11, 2002, now U.S. Pat. No. 6,758,806.

BACKGROUND

1. Field of the Invention

The invention relates to generally to intra-uterine devices, including hysteroscopes and related devices for microsurgical use such as use in the field of embryo implantation.

2. Description of the Related Arts

Improving the success of in vitro fertilization (IVF) depends on many factors, one of which is the delivery or transfer of the embryo to the endometrial lining of the uterus and the successful implantation of the embryo therein. It is well known in the art that assisting an embryo to adhere to, or implant within, a pre-determined area of the endometrial lining of the uterine wall, as opposed to simply releasing the embryo into the uterus, will enhance the success of IVF, minimize the risk of tubal pregnancies and reduce high-order multiple births.

U.S. patent application Ser. No. 09/759,415, filed Jan. 12, 2001, titled "Method and Apparatus for Assisted Embryo Implantation," describes a minimally invasive embryo transfer method, which, in one embodiment, describes a specially formed microcatheter to gently deliver one or more selected embryos into a pocket formed within the endometrial lining of a subject's uterus.

A microcatheter, such as described for use in the referenced document, is inserted typically by way of a hysteroscope. A hysteroscope is generally a specialized endoscopic device, for intrauterine use, which provides for direct or video observation of the interior of a subject's uterus and provides a platform for microsurgical instruments such as catheters by providing a channel or lumen through the device. Representative endoscopes are described in U.S. Pat. No. 6,006,002 issued to Motoki, et al.; U.S. Pat. No. 4,534,339 issued to Collins, et al.; and U.S. Pat. No. 4,203,430 issued to Takahashi. To enhance the field of vision of a hysteroscope within the uterus, often the uterus will be insufflated with a gas to distend the uterine walls. In addition to providing a channel or lumen through the device for instruments, prior art hysteroscopes may provide an additional channel or lumen for a gas introduction. A hysteroscopic device for performing a minimally invasive microsurgical intrauterine procedure such as an embryo implantation procedure should be small enough so that the subject's uterus may be accessed comfortably without inducing dilation. Multiple lumen devices tend to cause discomfort and are generally difficult to maneuver. What is needed is an improved endoscopic device that may provide a stable platform for use of such a microcatheter or other instrument.

SUMMARY OF THE INVENTION

A hysteroscope is disclosed. In one embodiment, a hysteroscope provides for minimally invasive operative access to the interior of the subject's uterus for instruments or insufflation via a single operative channel or lumen through an insertion arm of the device. To accomplish insufflation of a subject's uterus, a gas feed line is attached to a gas port on the hysteroscope which feeds into the operative channel. By using the same operative channel for gas insufflation and for instrument (e.g., microcatheter) insertion, the insertion arm of the hysteroscope may be minimized, permitting comfortable and easy uterine access as well as access without inducing dilation. Further features of embodiments of a hysteroscope described herein include an insertion arm having a distal tip with an edge radius that may tend to reduce the bluntness of the distal tip, and a hybrid rigid and flexible arm that may provide a more stable operative platform for microsurgery, such as the microsurgery of the endometrial lining and embryo implantation.

DETAILED DESCRIPTION

Figures 1, 2, 3:
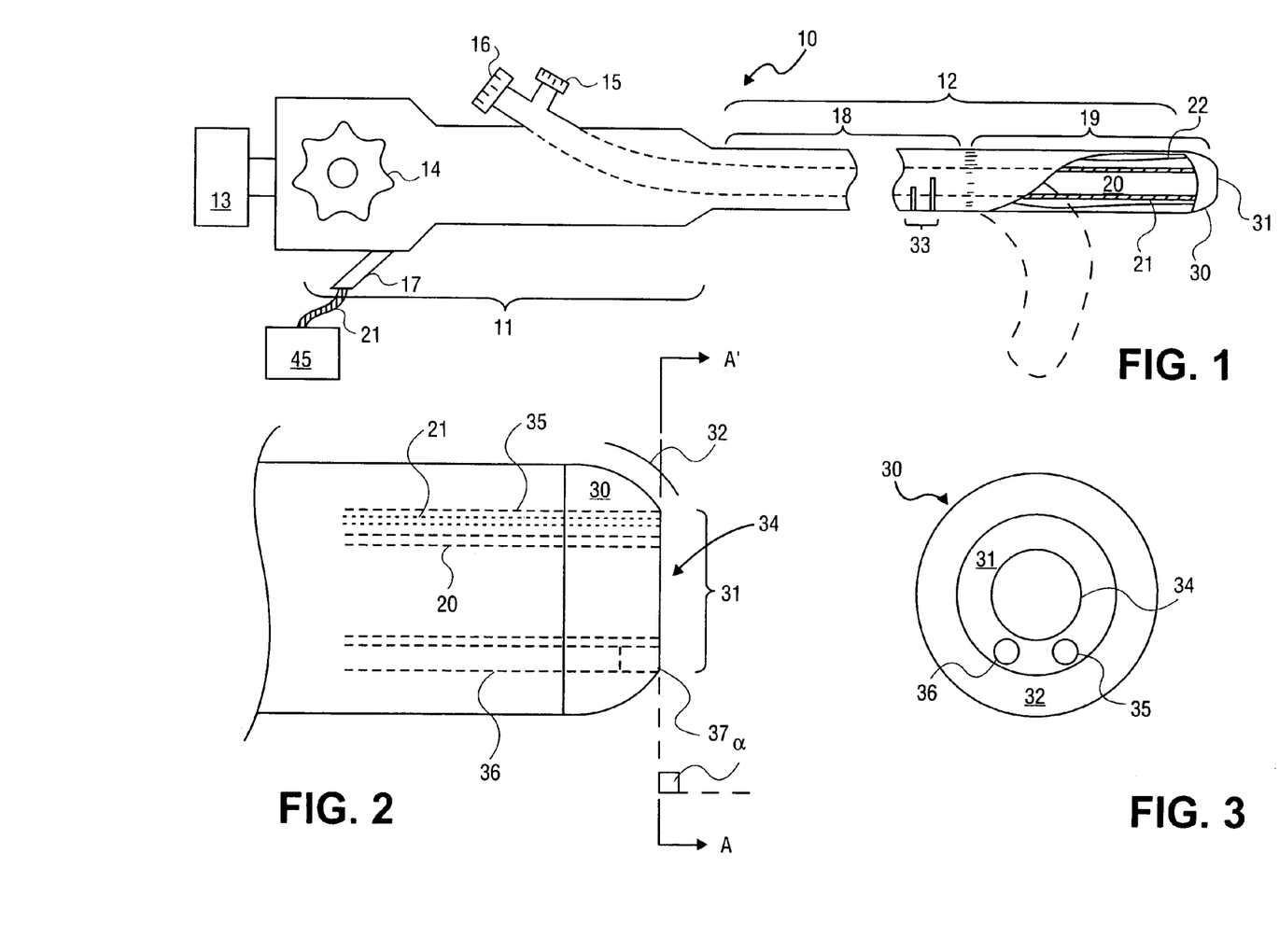
FIG. 1 is a schematic, cross-sectional side view of one embodiment of a hysteroscope.
FIG. 2 is a cross-sectional side view of a portion of the hybrid insertion arm portion of the hysteroscope of FIG. 1.
FIG. 3 is a cross-sectional view of the hysteroscope of FIG. 1 through line A–A' of FIG. 2.

Referring now to the drawings, illustrated in FIGS. 1–3 is one embodiment of a hysteroscope. During, for example, many types of embryo transfer procedures, hysteroscope 10 is inserted into a subject's uterus and used for direct, visual inspection of the endometrial lining and/or for embryo transfer or implantation.

Hysteroscope 10 is a two-part device, with operational section 11 at one end and hybrid insertion arm 12 at the other end. Operational section 11 is held by the operator during an intrauterine procedure, and a portion of hybrid insertion arm 12 is inserted into a subject's uterus. Supported on operational section 11 is eyepiece 13, used to visualize inside a uterus; control knob 14 used to maneuver a control structure (e.g., one or more braided wires extending to hybrid insertion arm 12 to actuate hybrid insertion arm 12 (the actuation shown in ghost lines)); and a series of access ports 15–17 extending from operational section 11 through one or more lumens inside both proximal portion 18 and distal portion 19 which form hybrid insertion arm 12. Hybrid insertion arm 12 is, in this embodiment, generally tubular and includes proximal portion 18 of a generally rigid material and distal portion 19 of a relatively flexible material (e.g., a polymer material).

The one or more lumens defined by access ports 15–17 extend through proximal portion 18 and distal portion 19 and exit or terminate at distal end 30 of distal portion 19 through guide face 31. Included among the one or more lumens is operative channel or lumen 20. Operative channel 20 extends between distal end 30 and, representatively access port 16. Operative channel 20 has a diameter suitable for insertion of a microcatheter therethrough for the purpose of performing a microsurgical procedure.

In one embodiment, distal end 30 of hybrid insertion arm 12 has edge radius 32 (e.g., a rounded edge) to facilitate gradual and gentle insertion through a subject's cervix. Edge radius provides less trauma than a blunt ended instrument and is generally able to gain entry into a smaller opening than a blunt instrument. To further aid the operator during insertion, series of locator marks 33 may be added to an exterior of hybrid insertion arm 12 to help the operator gauge the position of hybrid insertion arm 12 within a subject's uterus.

Prior art hysteroscopes with wholly flexible insertion sections are often difficult to control precisely during an intrauterine procedure. In the case of an intrauterine microsurgical procedure, hybrid insertion arm 12, having, in one embodiment, a rigid tubular proximal portion 18, preferably constructed of a smooth material such as stainless steel, seamlessly grafted/bonded to flexible tubular polymer (plastic-like) distal portion 19, is more easily maneuvered within a uterus and provides a more stable platform from which to perform the microsurgery and/or embryo implantation than from a wholly flexible hysteroscopic insertion arm.

Hybrid insertion arm 12 with both rigid proximal portion 18 and flexible distal portion 19 may be attached to a variety of hysteroscopic devices and should not be limited to being attached to, or supported by, operational section 11 detailed herein.

Often during an intrauterine procedure, uterine insufflation is desirable. Referring to FIG. 1, illustrated in hysteroscope 10 is gas port 15 which feeds into operational port 16 to operational channel 20. By sharing operational channel 20 between instruments and insufflation gas, a diameter of insertion arm 12 may be minimized yet providing the insufflation function.

Illumination within a subject's uterus may be added via illumination train extending through lumen 35 of hysteroscope 10. Lumen 35 extends, in one embodiment shown in FIGS. 1–3, between operational section 11 and hybrid insertion arm 12. Access to lumen 35 is provided by light port 17 where a light source may be coupled, preferably remotely so as not to hinder an operator's maneuvering of the device. Representatively, one or more illumination fibers 21 may extend a sufficient distance in a proximal direction from access port 17 and be coupled to light source 45 at its proximal end, so that light source 45 may remain stationary (e.g., on a table top), while hysteroscope 10 is maneuvered. In one embodiment, one or more illumination fibers 21 is inserted through lumen 35 and terminates at distal end 30. In one embodiment, one or more illumination fibers 21 includes a distal end of ground glass with a blunt or, as viewed, vertical cross-section. Preferably, the distal end of one or more illumination fibers 21 aligns (is co-extensive with) distal end 30. Accordingly, in the embodiment where distal end 30 has a rounded edge, such rounded edge, in one embodiment, does not include the entire cross-section of distal end 30. Referring to FIG. 2 and FIG. 3, guide face 31 has a blunt or, as viewed, a vertical profile ($\alpha$ of 90°). In this embodiment, operational channel 20 and lumen 35 are disposed within a cross-section of guide face 31.

In addition to an illumination train, hysteroscope 10 includes an image train. The visualization train includes lumen 36 extending between operational section 11 and hybrid insertion arm 12. At the operational section end, eyepiece 13 is disposed within or coupled about lumen 36. A video camera may alternatively be coupled about lumen 36 to provide video images of the uterus. At the hybrid insertion arm end, one or more lenses 37 is/are disposed within or coupled about lumen 36. In the embodiment shown in FIGS. 1–3, lumen 36 including one or more lenses 37 is disposed within a cross-section of guide face 31. An optical fiber may be disposed within lumen 36 in between the viewing device (e.g., eyepiece 13) and one or more lenses 37.

Figure 4:
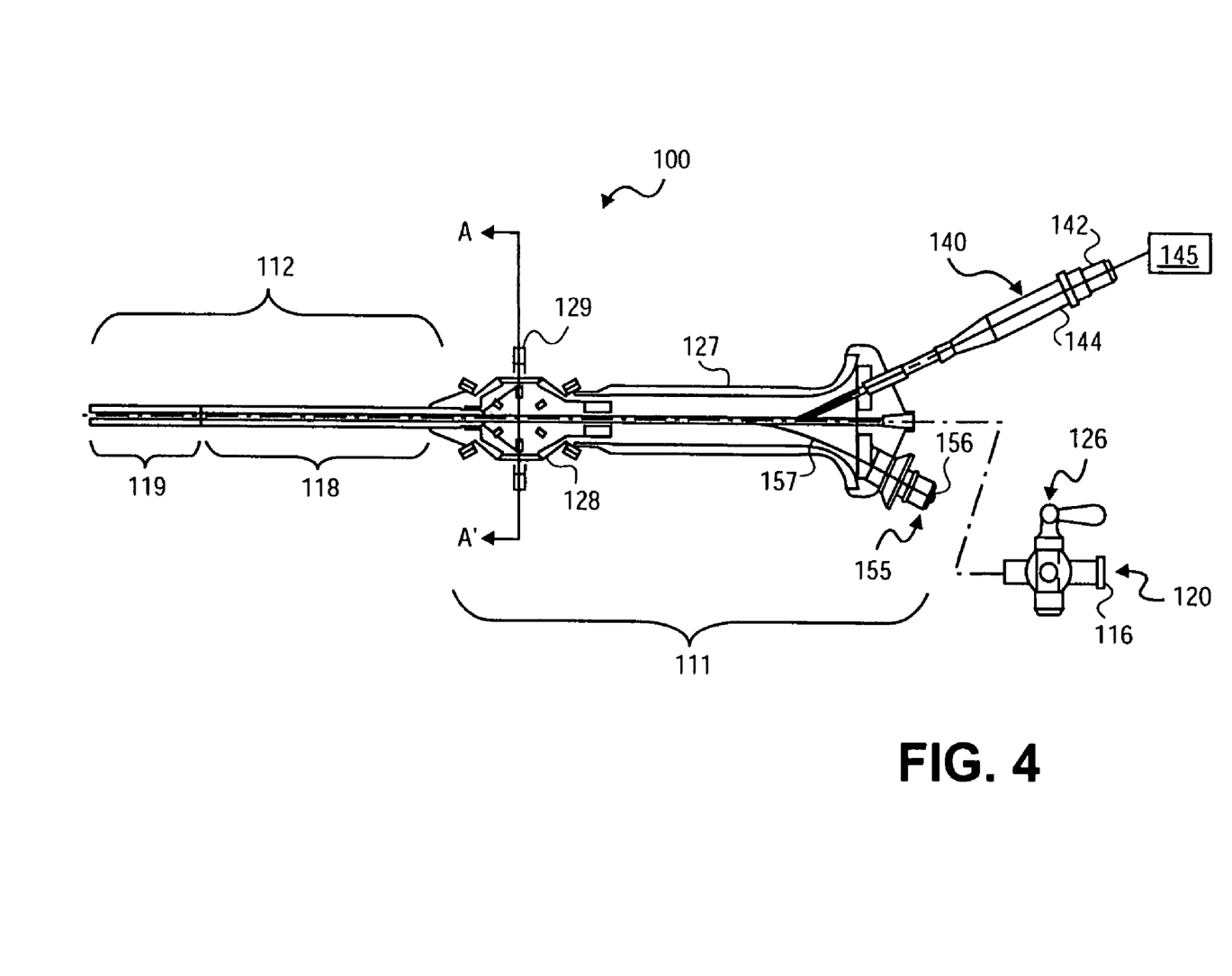
FIG. 4 is a schematic, cross-sectional side view of another embodiment of a hysteroscope.

FIG. 4 shows a schematic, cross-sectional view of another embodiment of a hysteroscope. In this embodiment, hysteroscope 100 includes operational section 111 at one end (a proximal end) and hybrid insertion arm 112 at a second end (a distal end). Hybrid insertion arm 112 is generally tubular (defining one or more lumens therethrough) and includes proximal portion 118 of a generally rigid material, such as stainless steel, and distal portion 119 of a relatively flexible material (e.g., a polymer material). Representatively, proximal portion 118 has a length on the order of about 8 to 10 cm with about an outside diameter (OD) on the order of 3 to 4 mm. Distal portion 119 has a representative length of 3 to 5 cm and a representative OD of 3 to 4 mm, preferably a representative length slightly smaller (at least toward distal end 130) than proximal portion 118.

Referring to FIG. 4, operational section 111 includes handle portion 127. Coupled to a distal end of handle portion 127 is lever holder 128. Disposed within lever holder 128 is articulating lever 129 that is coupled through, for example, wire or braided cable members to distal portion 119. Representatively, deflection of articulating lever 129 about lever holder 128 deflects distal portion 119 of hybrid insertion arm 112 to the same degree. In one embodiment, articulating lever 129 rotates about a single axis 60° in two directions (e.g., clockwise and counterclockwise) for a total range of deflection of 120°.

Figure 5:
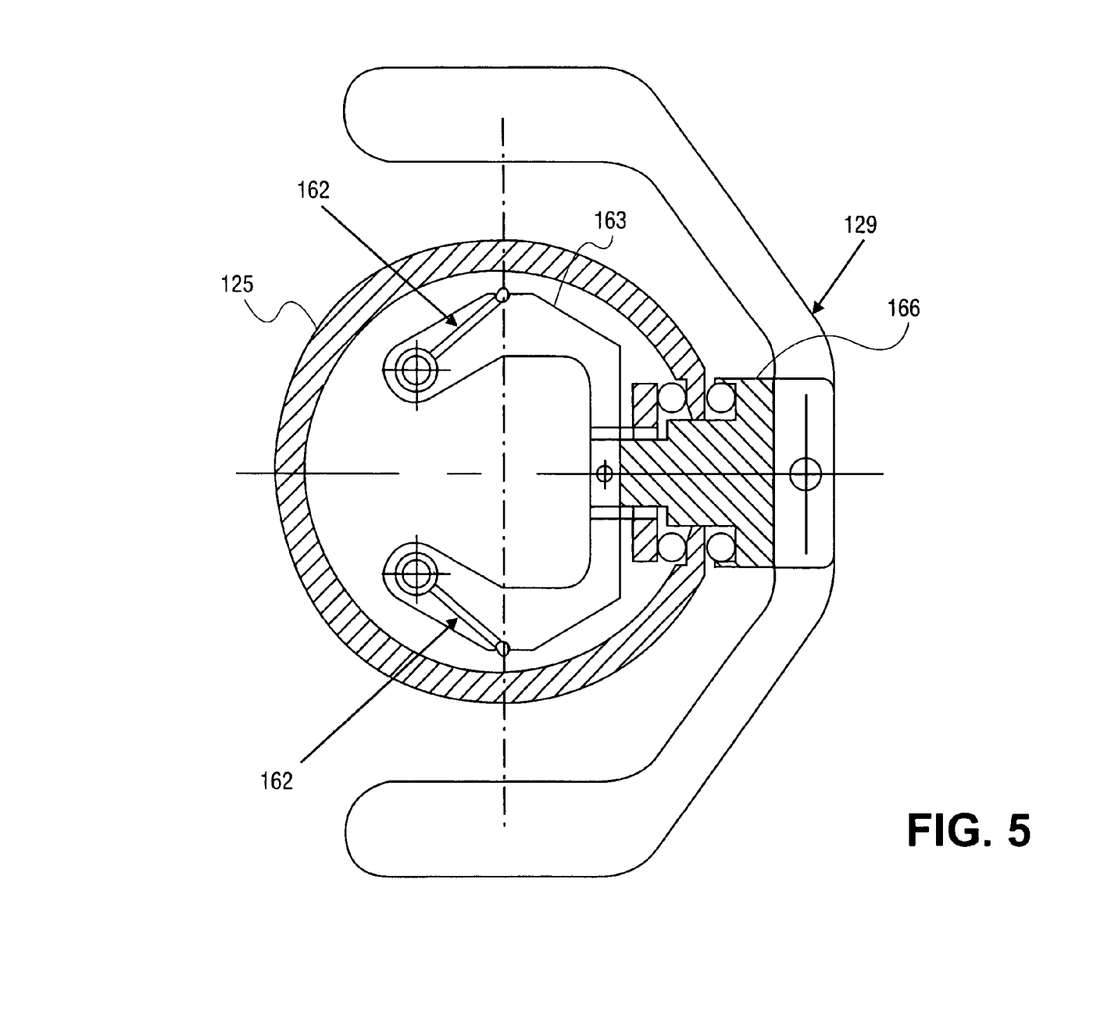
FIG. 5 is a partial cross-sectional view of the hysteroscope of FIG. 1 through line A–A'.

FIG. 5 shows a cross-section of lever holder 128 through line A–A' of FIG. 4. Lever holder 128 includes, in this embodiment, articulating lever 129 coupled to C-shaped wire mount 163 within primary lumen 125. As viewed, two wire members 162, such as braided wire members, are coupled to wire mount 163 at opposite sides thereof (e.g., 12 o'clock and 6 o'clock as viewed, respectively). Wire mount 163 is coupled to articulating lever 129 through lever holder 166.

Referring again to FIG. 4, at a proximal end of handle portion 127 of hysteroscope 100 is access port 116. Access port 116 provides access to operational channel or lumen 120. Operational channel 120 extends through the device from operational section 111 to hybrid insertion arm 112 terminating at distal tip 130. In this embodiment, access port 116 is axially aligned with operational channel 120. In one regard, the axial alignment aids the insertion of instruments such as a microcatheter into operational channel 120.

Also at a proximal end of handle portion 127 of hysteroscope 100 is a portion of illumination train 140 including illumination holder 144. A plurality of illumination fibers (e.g., glass fibers) are disposed within illumination holder 144 and join operational channel 120 within handle 127. As illustrated more clearly in FIG. 7 described below, in one embodiment, operational channel 120 and the plurality of illumination fibers are axially aligned and disposed within a primary lumen extending from operational section 111 to hybrid insertion arm 112. Light post 142 is disposed at a distal end of illumination holder 144 and may itself be a light source to the illumination fibers or be coupled to a light source. For example, light source 145 may be located remotely so as not to inhibit an operator's use of the device.

At a proximal end of illumination holder 144, the illumination fibers are surrounded by tubing or sheathing and the tubing or sheathing is coupled to handle portion 127.

Still referring to FIG. 4, at a proximal end of handle 127 is a portion of image train 155 including eyepiece 156. Eyepiece 156 is coupled to lumen 136 (see FIGS. 6 and 7) which joins operational channel 120 within handle 127 and is axially aligned within a primary lumen extending from operational section 111 to hybrid insertion arm 112.

Coupled at a proximal end of operational channel 120 is stopcock 126 to, in one position, seal or block operational channel 120 and, in another position, to allow insufflation gas or an instrument such as a microcatheter to be passed through operational channel 120. In another embodiment, stopcock 126 may have three positions to, for example, provide individual access ports for an instrument and for insufflation gas. In one embodiment, stopcock 126 is sterilizable and, where desired, removable and replaceable. A microcatheter and/or insufflation gas, in one embodiment, may alternatively be introduced to operational channel 120 at entry port 116.

Figure 6:
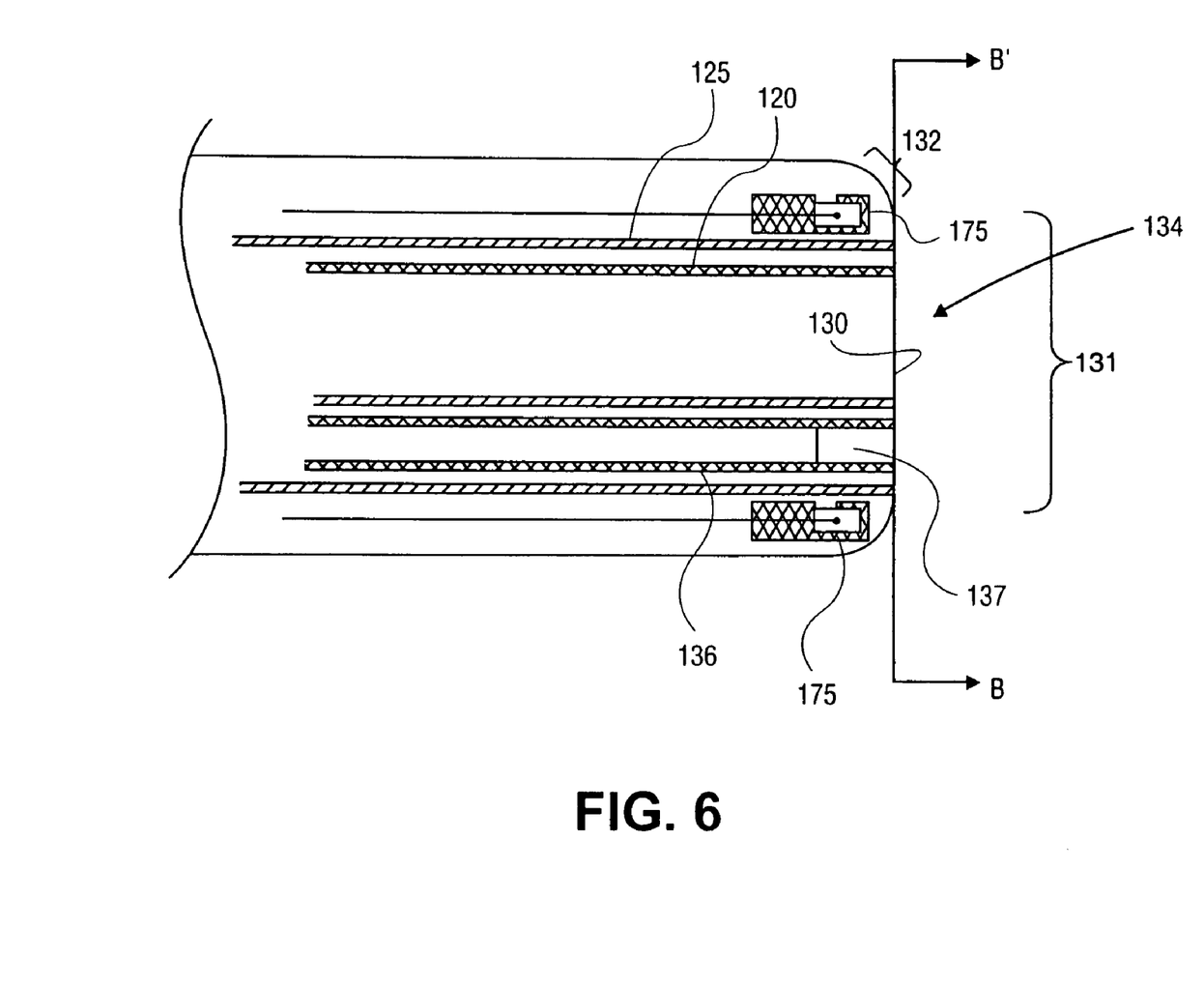
FIG. 6 is a cross-sectional side view of a portion of the hybrid insertion arm portion of the hysteroscope of FIG. 4.
Figure 7:
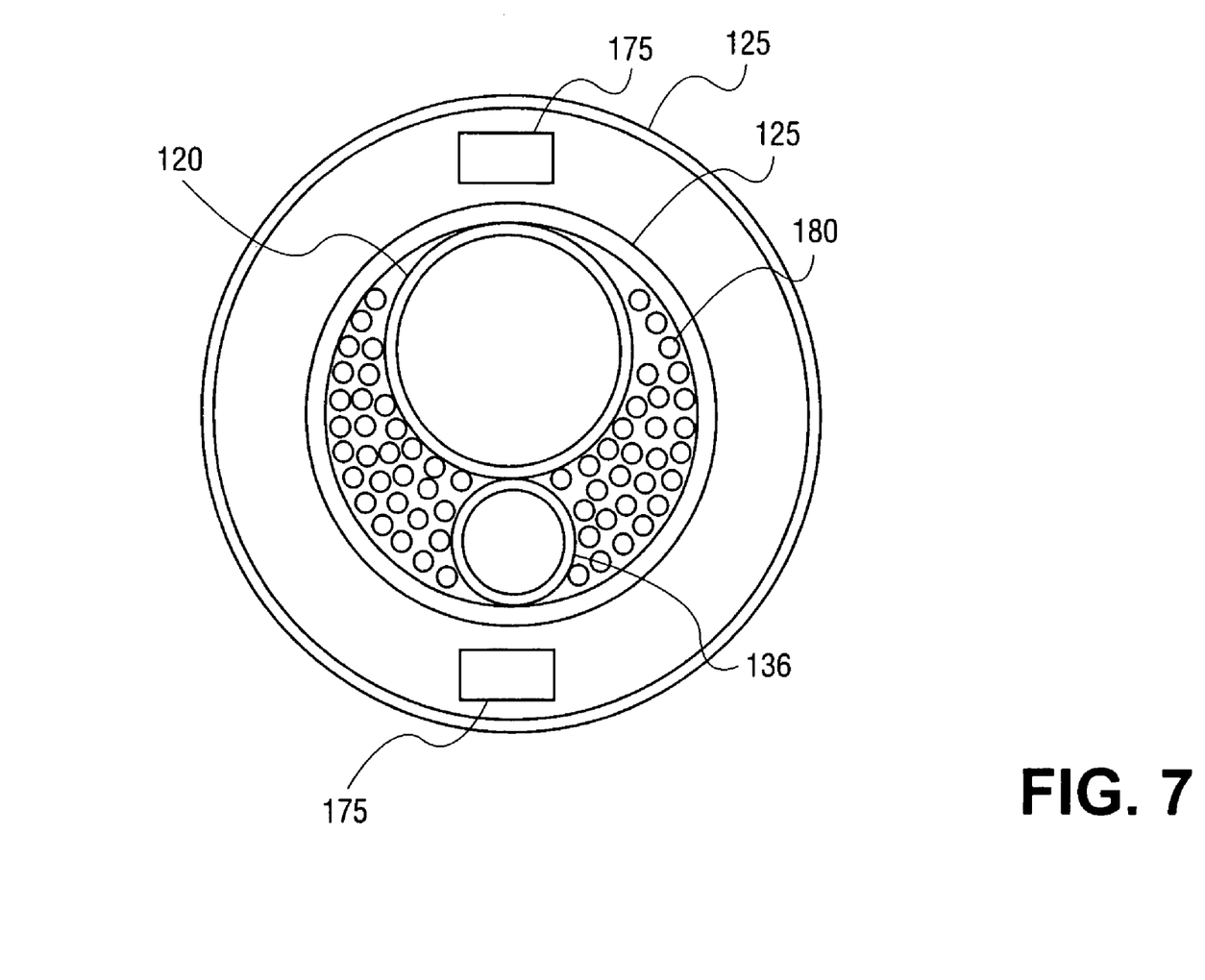
FIG. 7 is a cross-sectional view of the hysteroscope of FIG. 1 through line B–B' of FIG. 6.

FIG. 6 shows a schematic, cross-sectional side view of a distal end of hybrid insertion arm 112. FIG. 7 shows a cross-section through line B–B' of FIG. 6. Each figure shows primary channel 125 extending through hybrid insertion arm 112 to distal end 130. In one embodiment, primary channel 125 is a polymeric material of having a diameter on the order of 1.3 mm. Disposed within primary channel 125, in this embodiment, is operational channel 120 and illumination lumen 136. In a preferred embodiment, operational channel 120 has an inside diameter (ID) of about 1.5 mm or less, preferably 1.3 mm. Also disposed within primary channel 125 are a plurality of illumination fibers 180 (each having a representative diameter on the order of 0.12 mm) forming part of illumination train 140 extending back to illumination holder 144 and light post 142 and operational section 111. Still further disposed in operational channel 120 is image lumen 136 which forms part of image train 155 and is coupled, in one embodiment, to eyepiece 156 in operational section 111. Image fiber 157, such as a 10K image fiber may be disposed in image lumen 136 and coupled to eyepiece 156. At a distal end of image lumen 136 is one or more lenses 137, such as a GRIN, ILH-.5-WD15 lens.

Disposed outside of primary channel 125, preferably within a separate lumen or lumens or sheaths is co-axially disposed dumb bell 175 coupled (e.g., via adhesive) to distal end 130 of hybrid insertion arm 112. Wires 162 are coupled to dumb bell 175 to provide for articulation of distal portion 119 of hybrid insertion arm 112 by articulating lever 129.

Referring to FIG. 6, distal end 130 of hybrid insertion arm 112 has a rounded edge 132 and a blunt (e.g., vertical) guide face 131. Accordingly, guide face 131 has a smaller diameter than the outside diameter of distal portion 119 of hybrid insertion arm 112. It is appreciated that edge 132 need not be rounded but could be linearly-sloped. Primary channel 125 is disposed within blunt guide face 131 so that illumination fibers 180 (see FIG. 7) may terminate with a blunt edge at guide face 131. Rounded edge 132 facilitates insertion into a subject.

To minimize the diameter of the hybrid insertion arm described in the above embodiments, and to allow for a reduced diameter of the one or more lumens therethrough, including a reduced diameter of an operative channel of the hysteroscope, an improved microcatheter, representatively for use in embryo transfer, implantation and intrauterine microsurgery has been developed.

Figure 8:
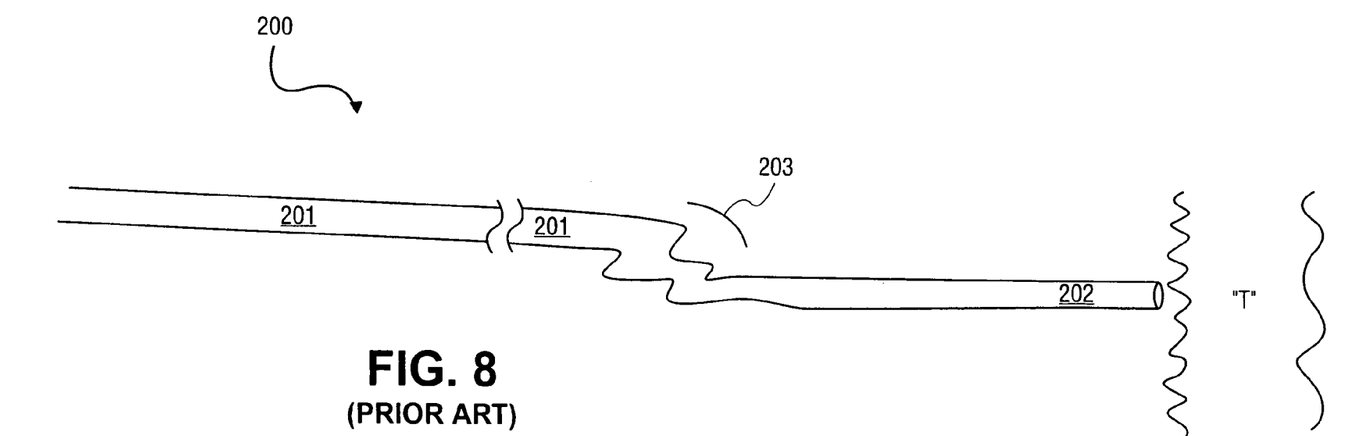
FIG. 8 is a side view of a prior art microcatheter.

A microcatheter is a flexible tube with a base section and a tip section. Shown in FIG. 8 is prior art microcatheter 200. Prior art microcatheter 200 includes proximal portion (base portion) 201 and distal portion (tip portion) 202 typically formed of the same extruded polymer (plastic) material. One such prior art microcatheter is embryo transfer catheter manufactured by Cook OB/Gyn of Spencer, Ind. However, when prior art microcatheter 100 is reduced to an outside diameter of less than 0.833 mm, it has been observed to be too flexible and become nonfunctional when it encounters tissue. Flexing is illustrated by reference numeral 203.

To overcome the flexibility problems, some manufacturers have produced "Teflon" based microcatheters which have greater wall strength and are less likely to bend. However, Teflon based microcatheters typically cannot be extruded with a tip diameter of less than 0.4 mm according to current techniques. Therefore, the trade-off for strength (rigidity) has been larger tip diameter.

Figure 9:
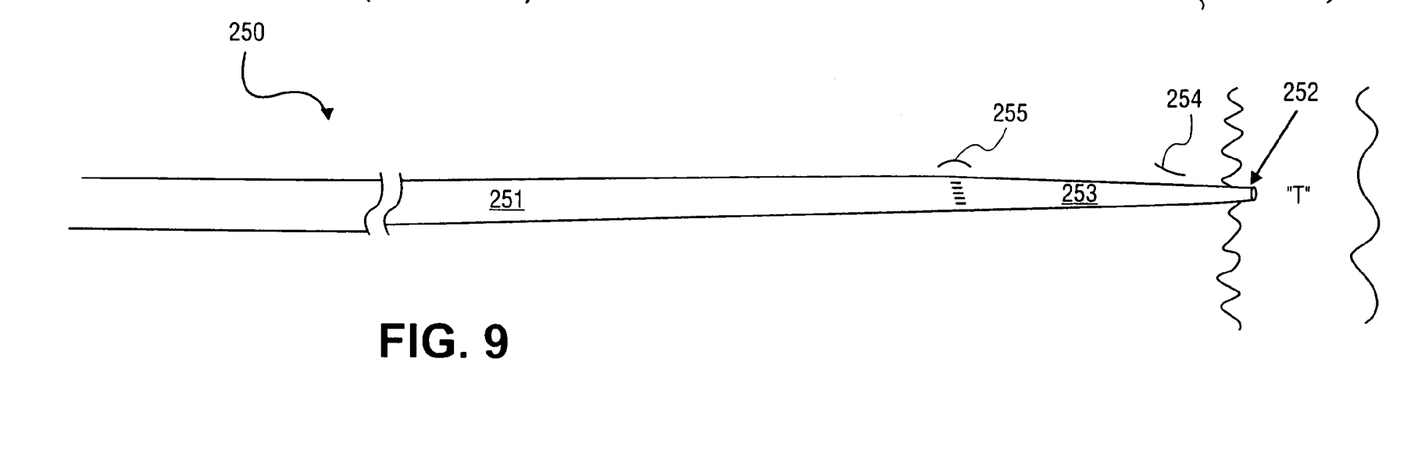
FIG. 9 is a side view of a hybrid microcatheter.

Referring to FIG. 9, microcatheter 250 includes, in one embodiment, a proximal portion (base portion) 251 of, for example, a polycarbonate material having a diameter of about one (1) mm or less that is resistant to flexing (bending) and distal portion (tip portion) 252 of, for example, transparent polycarbonate material that is generally non-toxic to embryos. Distal portion 253 includes, in one embodiment, tip 252 of an interior diameter of about 400 micrometers (μm). Distal portion 253 is similar, in one respect, to a micropipette and tapers 254 towards tip 252. Distal portion 253 and proximal portion 251 being of dissimilar, representatively extruded polymer materials, are bonded 255 together to form microcatheter 250. Bonding methods include a sonic weld, solvents, heat, adhesive and other suitable methods. Microcatheter 250 both resists bending when it encounters tissue and provides reduced diameter tip 252. Microcatheter 250 is also useful in-and-of-itself as a miniature microsurgical tool.

Figure 10:
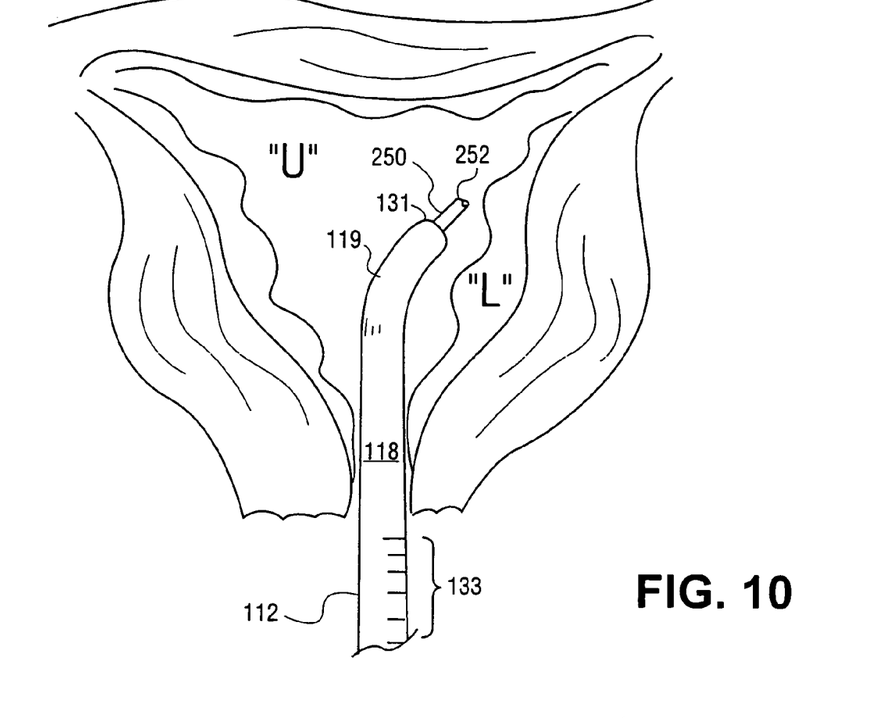
FIG. 10 is a first representative view of the hysteroscope being used for an embryo implantation procedure.
Figure 11:
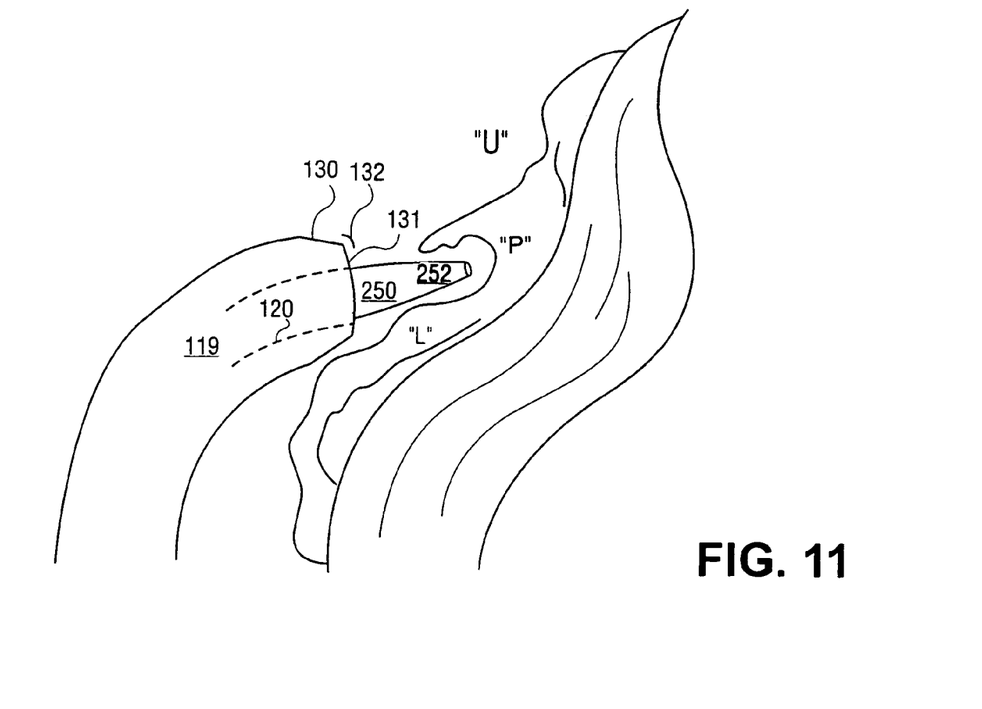
FIG. 11 is a second representative view of the hysteroscope being used for an embryo implantation procedure.

FIGS. 10 and 11 illustrate one embryo implantation procedure using, representatively hysteroscope 100 and microcatheter 250. During an embryo implantation procedure, entry port 116 of hysteroscope 100 receives microcatheter 250 which is of adequate length to allow distal end 251 thereof to extend from guide face 131. Hysteroscope 100 is inserted, either before or after receiving microcatheter 250, into a subject's uterus "U". Guide marks 133 on proximal portion 118 may be used as a reference for insertion depth. Light source 145 may illuminate a portion of the interior of the uterus and the portion of the uterus may be visualized by an operator through eyepiece 156. Articulating lever 129 may be used to maneuver/position a distal end of hysteroscope 100 (and possibly microcatheter 250) to a selected visualized position.

Distal end 521 of the microcatheter 250 once positioned within uterus "U" can be used to perform microsurgery such as the formation of an implantation pocket "P" within the endometrial lining "L" (FIG. 11). With an implantation pocket "P" formed in the endometrial lining "L", one or more embryos may be introduced through microcatheter 125.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. An apparatus comprising:
    a handle;
    a first elongate tubular body having a proximal end coupled to the handle and a distal end, the proximal end defining an entry port;
    a second tubular body, comprising a polymer material and having a proximal end and a distal end, the proximal end of the second tubular body coupled to the distal end of the first tubular body and a circumference of the distal end defining a guide face,
    wherein the first tubular body and the second tubular body are co-linearly aligned and collectively define a first lumen therethrough extending from the entry port to the guide face, the first lumen having a dimension adequate to accommodate in a co-linear alignment with the first tubular body:
        a second lumen having a dimension adequate to accommodate an instrument therethrough;
        at least one illumination fiber; and
        a third lumen comprising at least one lens disposed at the distal end of the second tubular body;
    wherein the second tubular body has a dimension adequate for insertion into a uterus of a human subject, and
    wherein the guide face comprises a blunt edge and an outside diameter less than an outside diameter of the second tubular body.

2. The apparatus of claim 1, wherein the handle has a proximal end and a distal end and the first tubular body extends through the handle, such that the entry port is disposed at the proximal end of the handle.

3. The apparatus of claim 1, further comprising:
    an articulating body coupled to the first tubular body and adapted to be articulated by an operator of the apparatus; and
    at least one wire coupled to the articulating body and to the distal end of the second body within the first lumen and outside the second lumen.

4. The apparatus of claim 3, wherein the articulating body is adapted to articulate the distal end of the second body up to 60° in at least two directions.

5. The apparatus of claim 3, wherein the articulating body is adapted to be articulated coaxially about the first tubular body.

6. The apparatus of claim 1, further comprising a light source coupled to the illumination fiber and disposed at a distance from the handle such that the handle may be maneuvered without a concomitant maneuvering of the light source.

7. The apparatus of claim 1, wherein the first tubular body comprises a metal material.

8. The apparatus of claim 1, further comprising a valve coupled to the entry port, the valve having at least one position providing access to the entry port.

9. The apparatus of claim 8, wherein the valve comprises a removable stopcock.

* * * * *